(12) United States Patent
Chapuis et al.

(10) Patent No.: US 7,886,367 B2
(45) Date of Patent: Feb. 15, 2011

(54) CLOSE-FITTING GARMENT

(75) Inventors: Serge Chapuis, Lepin le Lac (FR); Isabelle Roux, Metz-Tessy (FR)

(73) Assignee: Salomon S.A.S., Metz-Tessy (FR)

( * ) Notice: Subject to any disclaimer, the term of this patent is extended or adjusted under 35 U.S.C. 154(b) by 226 days.

(21) Appl. No.: 11/460,856

(22) Filed: Jul. 28, 2006

(65) Prior Publication Data

US 2007/0022510 A1 Feb. 1, 2007

(30) Foreign Application Priority Data

Jul. 29, 2005 (FR) .................................. 05.08103

(51) Int. Cl.
A41D 13/00 (2006.01)
A41D 13/06 (2006.01)

(52) U.S. Cl. .................................. 2/69; 2/22

(58) Field of Classification Search .............. 2/69, 2/227, 228, 239–242, 22
See application file for complete search history.

(56) References Cited

U.S. PATENT DOCUMENTS

| 2,144,514 | A | * | 1/1939 | Speh ............................ 2/87 |
| 2,177,543 | A | * | 10/1939 | Vecchi ......................... 2/46 |
| 4,783,858 | A | * | 11/1988 | Chevalier ..................... 2/90 |
| 5,154,690 | A |  | 10/1992 | Shiono |
| 5,367,708 | A |  | 11/1994 | Fujimoto |
| 5,447,462 | A | * | 9/1995 | Smith et al. ................. 450/122 |
| 5,640,714 | A |  | 6/1997 | Tanaka |
| 5,682,613 | A | * | 11/1997 | Dinatale ....................... 2/168 |
| 5,737,773 | A |  | 4/1998 | Dicker et al. |
| 5,887,453 | A | * | 3/1999 | Woods ......................... 66/171 |
| 6,018,819 | A | * | 2/2000 | King et al. ..................... 2/69 |
| 6,049,908 | A | * | 4/2000 | Bullock et al. ................. 2/69 |
| 6,127,595 | A | * | 10/2000 | Makoui et al. .............. 604/367 |
| 6,186,970 | B1 |  | 2/2001 | Fujii et al. |
| 6,216,495 | B1 |  | 4/2001 | Couzan et al. |
| 6,446,264 | B2 |  | 9/2002 | Fairhurst et al. |
| 6,878,647 | B1 | * | 4/2005 | Rezai et al. ................... 442/18 |
| 6,892,396 | B2 | * | 5/2005 | Uno et al. ..................... 2/115 |
| 2003/0167551 | A1 | * | 9/2003 | Findlay ......................... 2/93 |
| 2004/0111781 | A1 | * | 6/2004 | Miyake et al. ................ 2/69 |
| 2006/0085894 | A1 | * | 4/2006 | Yakopson et al. ............ 2/239 |
| 2006/0130215 | A1 | * | 6/2006 | Torry ........................... 2/227 |
| 2006/0156451 | A1 | * | 7/2006 | Klein et al. ................... 2/159 |
| 2007/0000010 | A1 | * | 1/2007 | Benini ........................... 2/69 |

(Continued)

FOREIGN PATENT DOCUMENTS

DE 10 2004 034 699 A1 4/2005

(Continued)

OTHER PUBLICATIONS

Patent Abstracts of Japan, vol. 13, No. 515 (C-655), published Nov. 17, 1989 (Japanese Patent Publ. No. 01-207403, publ. date Aug. 21, 1989).

*Primary Examiner*—Gary L Welch
*Assistant Examiner*—Amber R Anderson
(74) *Attorney, Agent, or Firm*—Greenblum & Bernstein, P.L.C.

(57) ABSTRACT

A sports garment made mainly of a laminate of a stretchable fabric and an elastic film. The elastic film is a PU, PVC, silicone film. The film is precut prior to laminating so as to provide ventilation zones on the fabric.

34 Claims, 3 Drawing Sheets

U.S. PATENT DOCUMENTS

2007/0226870 A1* 10/2007 Abbott .......................... 2/69
2008/0000003 A1* 1/2008 Melander ...................... 2/69

FOREIGN PATENT DOCUMENTS

| EP | 0 705 543 A1 | 4/1996 |
| EP | 1 016 351 A1 | 7/2000 |
| EP | 1 250 858 A1 | 10/2002 |
| FR | 2 548 892 A1 | 1/1985 |
| FR | 2 597 123 A1 | 10/1987 |
| JP | 01 207403 A | 8/1989 |
| WO | WO-98/18418 A1 | 5/1998 |
| WO | WO-98/36652 A2 | 8/1998 |

* cited by examiner

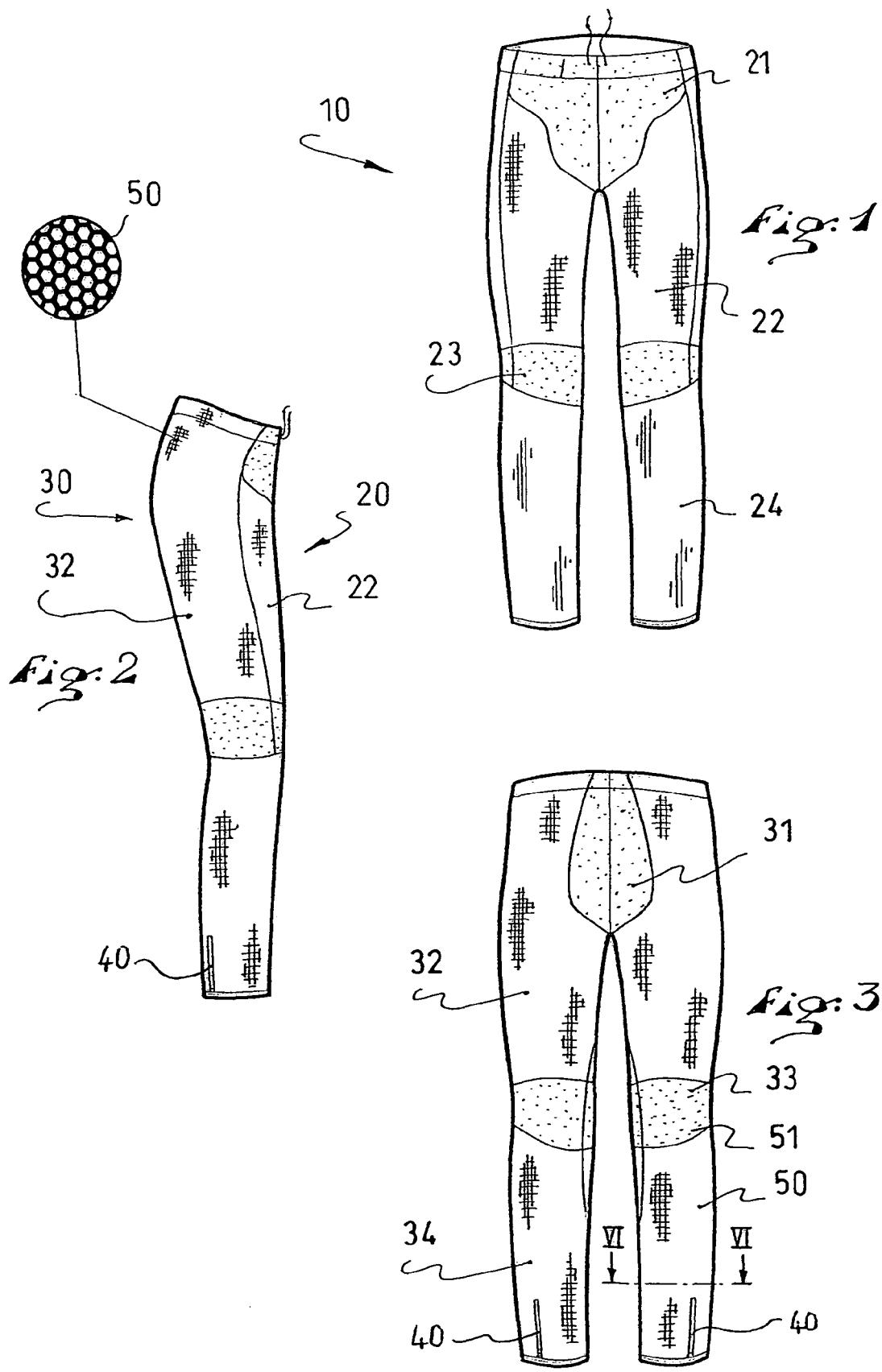

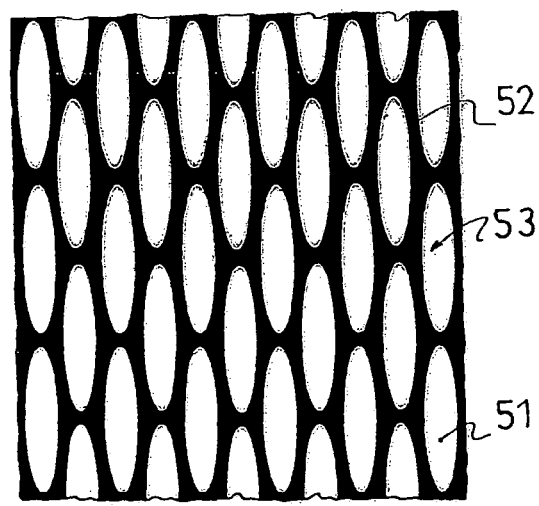
Fig. 5
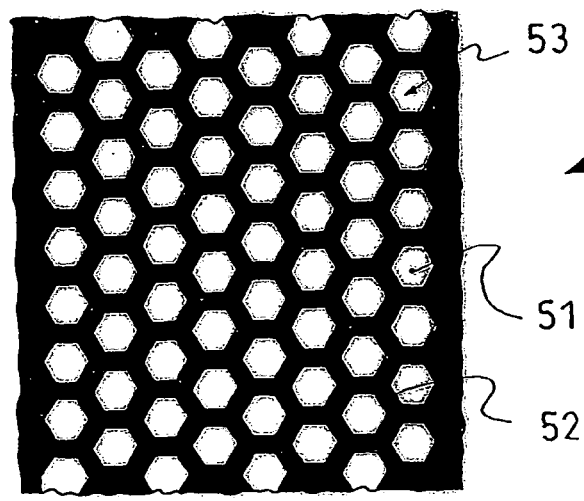
Fig. 4
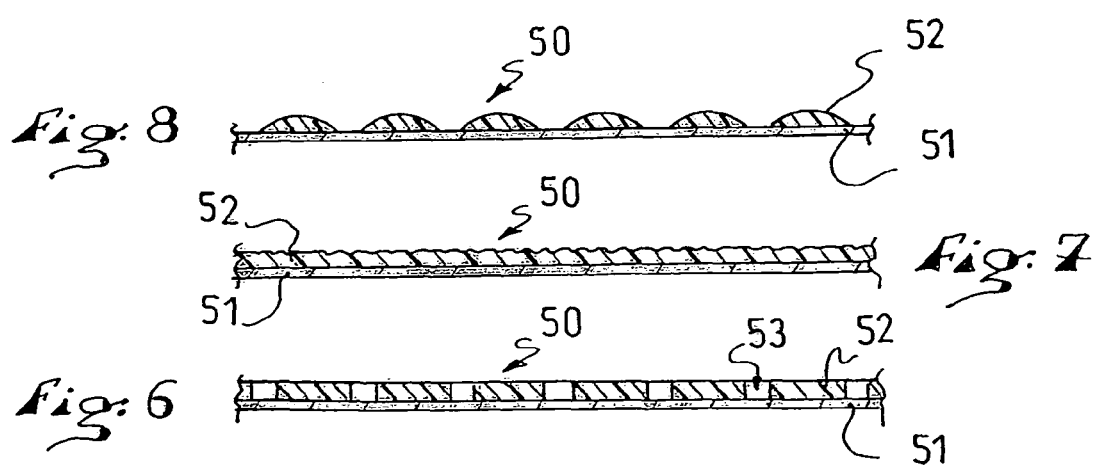
Fig. 8
Fig. 7
Fig. 6

CLOSE-FITTING GARMENT

CROSS-REFERENCE TO RELATED APPLICATION

This application claims priority under 35 U.S.C. §119 of French Patent Application No. 05.08103, filed on Jul. 29, 2005, the disclosure of which is hereby incorporated by reference thereto in its entirety.

BACKGROUND OF THE INVENTION

1. Field of the Invention

The invention relates to a garment, particularly a sports garment, which is close-fitting and designed to be worn on the upper and/or a lower part of the body.

2. Description of Background and Relevant Information

Garments of the aforementioned type are commonly used, for example, in the form of tights, which are worn on the lower part of the body for practicing foot race.

It is known from U.S. Pat. No. 5,367,708, for example, to design tight-fitting garments having portions made from a material that is less stretchable than others in predetermined areas of the garment, such less stretchable portions covering certain muscles, but not other muscles. This document also describes such a principle as adapted to garments in the form of T-shirts or socks. These known garments are in fact designed to provide a bandaging effect, with the function of supporting the muscles and joints involved for the purpose of preventing injuries.

The document EP 1 250 858, and family member U.S. Pat. No. 6,446,264, disclose making close-fitting garments, made of elastic panels joined by seams, the seams being arranged so as to reduce the stretchability of the panels and to increase the retaining/restraining effect. The garments have a very snug fit and are extremely difficult to put on. Indeed, any relative sliding of the garment with respect to the user's skin is to be avoided.

The document WO 98/36652 discloses making close-fitting garments made of an elastic base fabric, such as Lycra®, on which elastic resistance bands are sewn. These bands exert elastic resistance to movement so as to assist in building the body muscles.

It is also known from the French documents FR 2 548 892 and FR 2 597 123 to design restraining articles for medical or sporting use, constituted of elastic threads knitted according to a special process in order to achieve the desired degree of restraint. Such articles are adapted to improve blood circulation.

The document WO 98/18418, and family member U.S. Pat. No. 6,216,495, relate to a restraining stocking made of knitted elastic threads, which exert a more substantial restraining in the calf area than in the foot area, and is adapted more specifically to sporting activities.

This stocking is worn during and after the intense activity in order to improve the recovery, especially in the case of a long trip or a walk after the activity. By improving blood circulation, these restraining socks make it possible to substantially reduce cramps, dysesthesia, heaviness, and fatigue in the legs, and facilitate recovery after an intense activity.

SUMMARY OF THE INVENTION

The invention provides a close-fitting garment that improves blood circulation and facilitates recovery after an intense activity.

Further, the invention provides a close-fitting garment that procures a massaging effect.

Still further, the invention provides a close-fitting sports garment, which facilitates the manufacture and/or aesthetics thereof.

In this regard, a garment encompassed by the invention is a sports garment that includes a stretchable fabric/elastic film laminate in at least one zone of the garment surrounding an area of the body.

The fabric can be a conventional fabric such as jersey, a mesh with or without elastic fibers such as elastane, Lycra®, spandex, PBT, PET, whereas the elastic film can be a film of the PU type, such as a TEKFILM® film by Tradel, that is, made of a material with high elasticity properties.

The stretchable fabric/elastic film combination makes it possible to obtain a very elastic garment that can stimulate, support, and/or massage all of the muscles, as well as improve blood and lymphatic circulation when a restraining pressure is exerted.

Furthermore, the laminated structure allows the degree of elasticity of the garment to be very easily varied simply by varying the thickness, the type, or extent of coverage of the elastic film over a given surface.

The laminated structure, due to its modular design, makes it possible to change the manufacturing process very easily, inasmuch as simply changing the film or the cut thereof makes it possible, for a given base fabric pattern, to change the characteristics of the entire garment.

The manufacture is much simpler and flexible, since it does not require lengthy, difficult, and tedious adjustments to the knitting machines, as is the case with known restraining stockings.

Furthermore, gluing the elastic film, instead of sewing it, as in the document WO 98/36652, enables the garment to provide better comfort, without creating an uncomfortable "string effect".

The glue used for the laminated structure also contributes to the "elastic stiffness" or degree of restraint, or constraint, of the assembly.

The elastic film can be laminated in a continuous form, that is, without discontinuity. According to one embodiment, the elastic film is precut prior to laminating, that is, gluing, so as to constitute ventilation zones on the fabric.

These cuts can be made according to a repetitive and regular scheme, or pattern, so as to envelop and stimulate the muscles in a homogenous and uniform manner. Conversely, the cuts can be made according to an asymmetrical repetitive pattern so as to provide the garment with stiffness and restraining pressure that are more substantial along predetermined directions.

The laminated structure therefore also allows a very easy modification of the aesthetics of the garment by simply changing the film cutting pattern.

BRIEF DESCRIPTION OF DRAWINGS

The invention will be better understood and other characteristics thereof will become apparent from the description that follows, with reference to the annexed drawings, in which:

FIG. 1 is a front view of a pair of tights according to the invention;

FIG. 2 is a side view of the pair of tights of FIG. 1;

FIG. 3 is a rear view of the pair of tights of FIG. 1;

FIG. 4 shows a first cutting pattern for the elastic film;

FIG. 5 shows a second cutting pattern for the elastic film;

FIG. 6 is a cross-sectional view along the line VI-VI of FIG. 3;

FIG. 7 is a view, similar to FIG. 6, showing another embodiment;

FIG. 8 is a view, similar to FIG. 6, showing another embodiment;

DETAILED DESCRIPTION OF THE INVENTION

Figure 9:
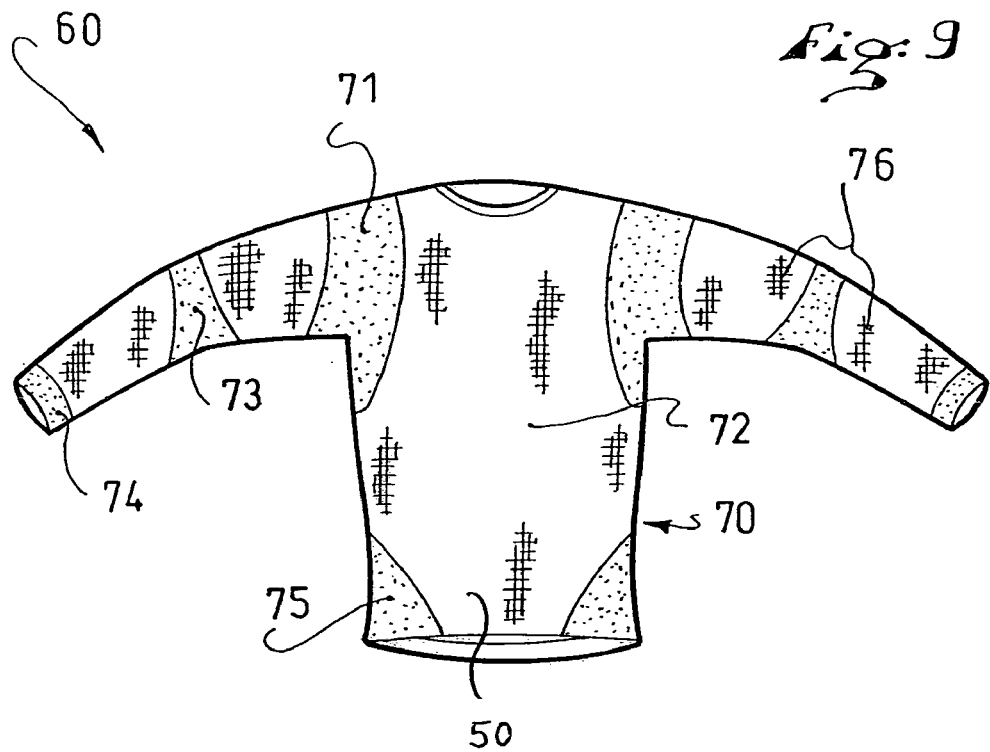
FIG. 9 is a front view of a T-shirt according to the invention.

FIGS. 1 to 3 show the invention as applied to a pair of tights 10 adapted particularly to foot racing, for example. The illustrated pair of tights has a "front" portion 20 shown in FIG. 1 and a "rear" portion 30 shown in FIG. 3.

As shown in these drawing figures, over the major part of their surface, including both front 20 and rear 30 portions, the pair of tights 10 is made of a laminate 50 according to the invention. That is, in FIGS. 1-3, the laminate is shown to extend throughout a majority of the garment.

As shown in FIG. 6, the laminate 50 is made of a first layer of fabric 51 and of a second layer of an elastic film 52, these two layers being glued to one another.

The fabric is jersey, a mesh made of cotton, polyester, polyamide, that is, any stretchable mesh. It can also be constituted of a fabric including elastic fibers such as elastane, Lycra®, spandex, PBT, PET. This material is a stretchable fabric due to its (jersey) construction, or to the fibers of which it is made. It is more or less elastic.

According to one embodiment of the invention, the invention is made of a ventilated mesh, net type of material, and/or a moisture-wicking material, and/or anti-microbial material such as X-Static®.

The elastic film 52 is PU film, for example, as sold under the tradename Tradel or Tekfilm® by Framis, or a PU film sold by Bemis. It can also be PVC or silicone.

Such PU films are made by coating superimposed polyurethane layers, the stratification making it possible to obtain an adhesive surface.

The elastic film made of PU, PVC, or silicone can also be applied directly without additional adhesive, for example, by coating or serigraphy. The film can be glued to the fabric by hot-pressing or can be directly laminated on the fabric.

In the example shown, the elastic film is a PU film. It is precut prior to gluing and therefore has cuts and openings 53. These openings 53 are shown in FIG. 6 as cutouts, i.e., through-openings extending through the elastic film 52.

These cuts 53 can have a polygonal shape, in this case hexagonal, as shown in FIGS. 1 to 3 and 4. This polygonal shape can be regular or symmetrical, so that the elastic constraint exerted by the PU film is regular.

The polygonal shape can also be asymmetrical, for example, rectangular, so that the elastic constraint is not uniform.

The cuts 53 can also have a curved, symmetrical shape, for example, circular, or asymmetrical, for example, elliptical, as shown in FIG. 5.

The cuts 53 make it possible to provide the entire garment with breathability, ventilation, since the base fabric 51 is not then covered and is apparent through these cuts.

If such breathability is not desired, for example, for a winter garment, one can provide the film 52 to be uniform, and therefore without any cuts, as shown in FIG. 7.

The PU film 52 can also be applied in the form of studs 52 (see FIG. 8), having hemispherical shapes or other shapes, which project with respect to the fabric layer 51 and can therefore procure a massaging effect. The massaging effect is also obtained with the cuts due to the relative sliding of the garment with respect to the user's skin.

In this case, the studs 52 are instead positioned within the garment. However, they can also be positioned outside.

In any case, the laminate also provides a very appreciable aesthetic/decorative effect. This effect can be reinforced by color effects (for example, by using an elastic film, the color of which is in contrast with the support fabric), imprint effects (colored and/or raised) of the elastic film; by also varying the thickness and/or the relief of the elastic film, etc. The elastic film could also be used to glue another fabric that is precut in the same manner in order to achieve a particular aesthetic effect. In this case, the elastic film is a double adhesion gluing film.

Similarly, the cutting patterns can be regular or irregular for equally aesthetic reasons.

In any case, the pattern of the garment, at least in the restraining areas, corresponds to smaller dimensions than those of the user's body, so that the fabric is tensioned when the garment is being put on and can exert the desired elastic restraining/massaging action.

Traction tests by means of a traction machine of the Adamel Lhomargy type have shown that merely gluing the PU film on a more or less stretchable material makes it possible to increase (in this case, to multiply by a factor of 3 in the example below), the elastic resistance of the fabric. The table below indicates the traction force values in N/an that must be applied for a fabric that is covered or not covered with an elastic film.

| Fabric | Alone | With Tradel ® elastic fabric |
| --- | --- | --- |
| Power Lycra ® | 1.44 | 4.5 |
| Malaga Lycra ® | 1.26 | 4.75 |

As shown in FIGS. 1 to 3, the laminate is interrupted in the areas of the garment corresponding to the greatest heat-generating parts of the body. In the example shown in FIGS. 1 to 3, these most homogenous areas, which therefore have no elastic film, are the front 23 and rear 33 articulation zones (i.e., joints), respectively, of the knees, and the front 21 and rear 31 zones of the pelvis, and, therefore, they only have the fabric layer 51. They can also be made of another, more ventilated fabric. The front 22 and rear 32 upper portions, the tibias 24 and calves 34 portions are therefore completely covered by the laminate 50 according to the invention. In other words, the thigh and the lower leg are completely surrounded or enveloped by the laminate.

In the exemplary embodiment shown in FIGS. 1-3, the garment 10 can be said to include a limb portion, i.e., that which extends longitudinally, along a length of either of the legs of the wearer, with such limb portion extending lengthwise across a joint portion of the garment, i.e., longitudinally from a first side of the knee (such as the upper side) to a second side of the knee. Although the garment extends across the knee joint, the laminate, or garment composite (i.e., a type of elastic constraint arrangement), is interrupted at joint portion, although the laminate is shown to extend completely around the leg of the wearer (i.e., around the limb portion of the garment), i.e., the laminate/composite forms a tubular portion around the leg of the wearer.

Zippers 40, or other types of slide fasteners, are provided at the lower end of the calves 34 for opening the tight-fitting portion at the lower part of the legs and for enabling it to be easily put on. A zipper, or slide fastener, can also be provided on the front of the garment and/or can be replaced with other types of closure means, such as snap fasteners, buttons, etc.

Figure 10:
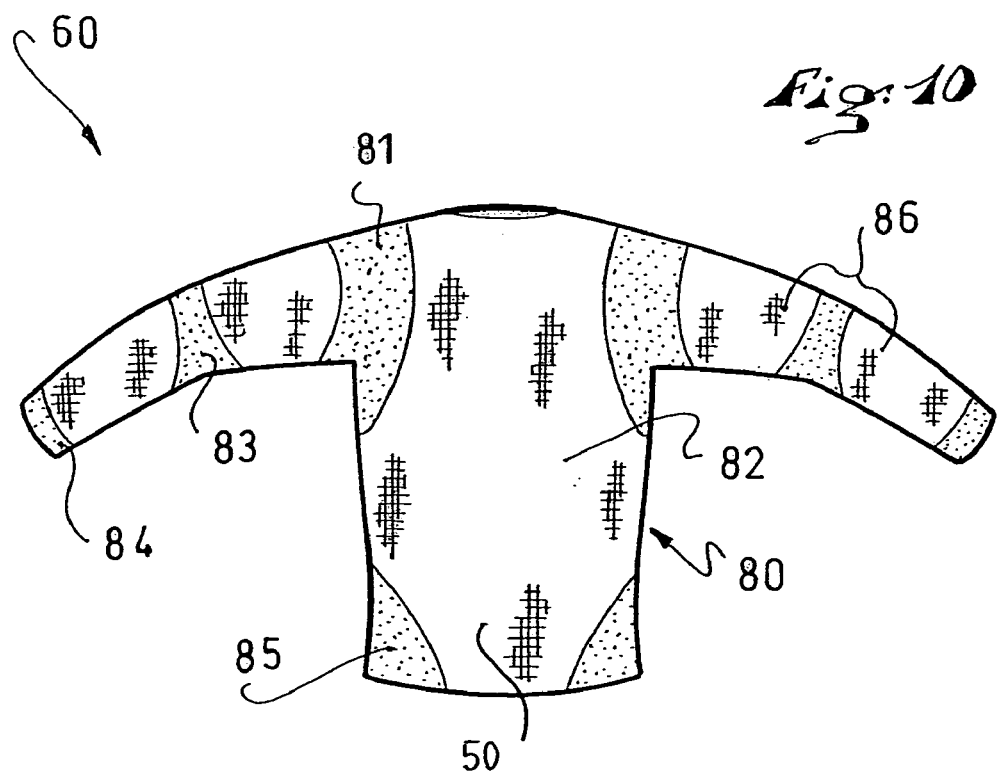
FIG. 10 is a rear view of the T-shirt of FIG. 9.

FIGS. 9 and 10 show the invention as applied to a long-sleeved T-shirt 60 and respectively illustrate a front portion 70 and a rear portion 80 thereof.

In this case, the laminate 50 completely covers and envelops the front 72 and back 82 of the torso, as well as the front 76 and rear 86 zones, respectively, of the arms and forearms. As mentioned in connection with the tights illustrated in FIGS. 1-3, the laminate is shown to extend throughout a majority of the shirt shown in FIGS. 9 and 10.

As in the preceding case, the laminate 50 is interrupted in the areas of the garment corresponding to the areas of the body that generate the most heat; in this case, the elbows 73, 83, the armpit/shoulder joint zones 71, 81, the zones 74, 84 of the wrist, and the lateral portions 75, 85 of the waist, and is replaced in these areas by a more ventilated fabric.

The invention is not limited to the particular embodiments illustrated and described hereinabove by way of non-limiting examples, and can also be applied to other garments, particularly short-sleeved T-shirts, jerseys, etc., without leaving the scope of the invention.

It is also possible to laminate the elastic film on only some portions of the garment, depending upon the degree of restraint and/or technical specifications of the garment desired on the corresponding parts of the body.

In the case of a pair of tights, for example, the invention encompasses having the restraining effect only in the calf area, where the restraining effect is important for blood circulation, and the laminating will only be undertaken on the leg, that is, the portion extending from the knee to the foot. One can also provide for a restraining or a massaging effect only in the thigh areas, etc.

The invention claimed is:

1. A sports garment comprising:
a limb portion for extending along a length of a limb of the wearer, said limb portion extending lengthwise across a joint portion;
a laminate comprising a stretchable fabric/elastic film located in at least one area of the garment, the garment adapted for a tight fit around a torso, abdomen, and arms or legs of a wearer;
the laminate extending completely around the limb portion of the garment to form a tubular portion;
the laminate including a lengthwise extension along the limb, said lengthwise extension of the laminate not extending lengthwise across the joint portion of the limb portion of the garment;
said elastic film being directly affixed to the stretchable fabric;
said elastic film having a plurality of cutouts arranged in said elastic film according to a repetitive pattern;
the laminate extending throughout a majority of the garment.

2. A sports garment according to claim 1, wherein:
the elastic film comprises a film consisting of one of PU, PVC, and silicone.

3. A sports garment according to claim 1, wherein:
the elastic film is a continuous film.

4. A sports garment according to claim 1, wherein:
the film is precut prior to laminating to provide ventilation zones on the fabric.

5. A sports garment according to claim 4, wherein:
the cuts demarcate holes having a curved periphery.

6. A sports garment according to claim 1, wherein:
the cuts demarcate polygonal holes.

7. A sports garment according to claim 1, wherein:
the film is applied in the form of studs.

8. A sports garment according to claim 1, wherein:
areas of the garment adapted to generate the most heat by the wearer do not include the film.

9. A sports garment according to claim 1, wherein:
the fabric is ventilated.

10. A sports garment according to claim 1, wherein:
the garment is a pair of tights;
the laminate covers at least a leg portion of the pair of tights.

11. A sports garment according to claim 1, wherein:
the elastic film is located in at least one zone of the garment adapted to surrounds an area of the body.

12. A sports garment according to claim 1, wherein:
the stretchable fabric extends lengthwise across the joint portion of the limb portion of the garment.

13. A sports garment according to claim 1, wherein:
the cutouts extend to an outer surface of the garment.

14. A sports garment comprising:
a limb portion for extending along a length of a limb of the wearer, said limb portion extending lengthwise across a joint portion;
a stretchable fabric providing the garment with a tight fit around a torso, abdomen, and arms or legs of a wearer;
the stretchable fabric extending completely around the limb portion of the garment to form a tubular portion;
an elastic constraint arrangement directly affixed to the stretchable fabric, both the elastic constraint arrangement and the stretchable fabric extending throughout a major extent of the garment;
the elastic constraint arrangement includes a lengthwise extension along the limb, the lengthwise extension of the elastic constraint arrangement not extending lengthwise across the joint of the limb portion of the garment;
said elastic constraint arrangement comprising a repetitive scheme of polygonal, elliptical, or circular cutouts.

15. A sports garment according to claim 14, wherein:
said elastic constraint arrangement comprises an elastic film laminated to said stretchable fabric, said cutouts having been pre-cut prior to lamination.

16. A sports garment according to claim 14, wherein:
the stretchable fabric extends lengthwise across the joint portion of the limb portion of the garment.

17. A sports garment according to claim 14, wherein:
the stretchable fabric extends lengthwise from a first laminate portion on a first side of the joint portion of the limb portion of the garment, across the joint portion, and to a second laminate portion on a second side of the joint portion of the limb portion of the garment.

18. A sports garment according to claim 14, wherein:
the joint portion is a knee joint.

19. A sports garment according to claim 14, wherein:
the joint portion is an elbow joint.

20. A sports garment according to claim 14, wherein:
the cutouts extend to an outer surface of the garment.

21. A garment comprising:
a stretchable fabric providing the garment with a tight fit around portions of a wearer's body, said portions comprising limb portions and joint portions, each of said limb portions extending lengthwise across a respective one of said joint portions;
the stretchable fabric extending completely around the limb portions of the garment to form tubular portions;
an elastic constraint arrangement affixed to the stretchable fabric, the elastic constraint arrangement and stretchable fabric comprising a garment composite;

said garment composite constituting a majority of an outer surface area of the garment;

said garment composite includes a lengthwise extension extending along said limb portions and being interrupted in at least a plurality of said joint portions;

wherein the lengthwise extension of the garment composite not extending lengthwise across the joint of the limb portion of the garment said elastic constraint arrangement comprising a repetitive scheme of ventilation openings.

22. A garment according to claim 21, wherein:
said elastic constraint arrangement comprises an elastic film laminated to said stretchable fabric.

23. A garment according to claim 21, wherein:
said limb portions comprise leg portions or arm portions.

24. A garment according to claim 21, wherein:
said joint portions comprise leg/pelvis joints or arm/shoulder joints.

25. A garment according to claim 23, wherein:
said joint portions comprise knee joints or elbow joints.

26. A garment according to claim 21, wherein:
the ventilation openings extend to the outer surface area of the garment.

27. A garment according to claim 21, wherein:
the elastic constraint arrangement is directly affixed to the stretchable fabric.

28. A garment comprising:
a limb portion for extending along a length of a limb of the wearer, said limb portion structured and arranged to extend lengthwise along a wearer's limb;

said limb portion comprising a joint portion structured and arranged to extend lengthwise along the wearer's limb across a wearer's joint;

a stretchable fabric providing the garment with a tight fit around portions of a wearer's body, said portions comprising said limb portion and said joint portion;

an elastic constraint arrangement affixed to the stretchable fabric, the elastic constraint arrangement and stretchable fabric comprising a garment composite;

said garment composite being structured and arranged to extend around the wearer's limb to form a tubular portion;

said tubular portion of said garment extending lengthwise along the wearer's limb, said tubular portion being interrupted in at least said joint portion, whereby said tubular portion does not extend lengthwise across said joint portion of said limb portion of the garment;

said elastic constraint arrangement comprising a repetitive scheme of ventilation openings.

29. A garment according to claim 28, wherein:
said garment composite constitutes a majority of an outer surface area of the garment.

30. A garment according to claim 28, wherein:
said elastic constraint arrangement comprises an elastic film laminated to said stretchable fabric.

31. A garment according to claim 28, wherein:
the stretchable fabric extends lengthwise across the joint portion of the limb portion of the garment.

32. A garment according to claim 28, wherein:
the stretchable fabric extends lengthwise from a first garment composite portion on a first side of the joint portion of the limb portion of the garment, across the joint portion, and to a second garment composite portion on a second side of the joint portion of the limb portion of the garment.

33. A garment according to claim 28, wherein:
the joint portion is a knee joint portion.

34. A garment according to claim 28, wherein:
the joint portion is an elbow joint portion.

* * * * *